United States Patent
Ihara et al.

(10) Patent No.: US 8,272,270 B2
(45) Date of Patent: Sep. 25, 2012

(54) ULTRASONIC MEASUREMENT WAVEGUIDE ROD AND ULTRASONIC MEASUREMENT INSTRUMENT

(75) Inventors: Ikuo Ihara, Nagaoka (JP); Motonori Kawasaki, Nagaoka (JP)

(73) Assignee: Nagaoka University of Technology, Niigata (JP)

( * ) Notice: Subject to any disclaimer, the term of this patent is extended or adjusted under 35 U.S.C. 154(b) by 304 days.

(21) Appl. No.: 12/741,277

(22) PCT Filed: Nov. 7, 2008

(86) PCT No.: PCT/JP2008/070348
§ 371 (c)(1),
(2), (4) Date: Jun. 18, 2010

(87) PCT Pub. No.: WO2009/063812
PCT Pub. Date: May 22, 2009

(65) Prior Publication Data
US 2011/0023612 A1    Feb. 3, 2011

(30) Foreign Application Priority Data
Nov. 15, 2007  (JP) .................. 2007-297307

(51) Int. Cl.
*G01N 29/00* (2006.01)
(52) U.S. Cl. .......................... 73/632; 73/628
(58) Field of Classification Search .............. 73/632, 73/628, 644, 861.18, 861.25–861.29; 310/334
See application file for complete search history.

(56) References Cited

U.S. PATENT DOCUMENTS

| | | | | |
|---|---|---|---|---|
| 4,336,719 A | * | 6/1982 | Lynnworth | 73/861.27 |
| 4,635,198 A | * | 1/1987 | Hohlweck et al. | 600/448 |
| 5,022,014 A | * | 6/1991 | Kulczyk et al. | 367/87 |

(Continued)

FOREIGN PATENT DOCUMENTS
JP    59-180456    10/1984
(Continued)

OTHER PUBLICATIONS

Ihara, Ikuo, et al., "Ultrasonic In-line Sensors for inclusion Detection in Liquid Metals", 2002 IEEE Ultrasonics Symposium Proceedings, 2002, vol. 1, pp. 811-814.

*Primary Examiner* — J M Saint Surin
(74) *Attorney, Agent, or Firm* — Boyle Fredrickson, S.C.

(57) ABSTRACT

An ultrasonic measurement waveguide rod which is easy to manufacture and is capable of preventing a noise echo. An ultrasonic flaw detection waveguide rod 2 is arranged with a probe on one axial end thereof and a contact surface to be brought into contact with a test piece on the other end thereof. The cross-sectional shape of the rod 2 perpendicular to the axial direction is a polygon having sides any one (41A) of which is not parallel to any of the other sides 41B, 41C, 41D. Since at least a pair of the sides 41A, 41C opposed to each other are not parallel to each other, an ultrasonic wave P is allowed to reflect off outer surfaces making up the nonparallel sides 41A, 41C, enabling the ultrasonic wave P to be prevented from returning to the probe 3 as a noise echo. For example, the ultrasonic wave component reflected perpendicularly by one outer surface is reflected by the opposite outer surface and travels toward the outer surface having the side 41D. Hence, an echo or a noise hardly returns to the probe.

20 Claims, 8 Drawing Sheets

U.S. PATENT DOCUMENTS

| | | | |
|---|---|---|---|
| 5,241,287 A * | 8/1993 | Jen | 333/143 |
| 6,047,602 A * | 4/2000 | Lynnworth | 73/632 |
| 6,425,906 B1 * | 7/2002 | Young et al. | 606/169 |
| 6,856,712 B2 * | 2/2005 | Fauver et al. | 385/12 |
| 6,889,552 B2 * | 5/2005 | Nguyen et al. | 73/632 |

FOREIGN PATENT DOCUMENTS

| | | |
|---|---|---|
| JP | 63-117735 | 5/1988 |
| JP | 03-081662 | 4/1991 |
| JP | 03-114450 | 5/1991 |
| JP | 08-021828 | 1/1996 |
| JP | 09-184827 | 7/1997 |
| JP | 2001-264304 | 9/2001 |
| JP | 2002-250719 | 9/2002 |
| JP | 2007-212358 | 8/2007 |

* cited by examiner

ULTRASONIC MEASUREMENT WAVEGUIDE ROD AND ULTRASONIC MEASUREMENT INSTRUMENT

TECHNICAL FIELD

The present invention relates to an ultrasonic measurement waveguide rod used for an ultrasonic measurement test such as ultrasonic flaw detection test.

BACKGROUND ART

An ultrasonic flaw detection test, as one of ultrasonic measurement tests, is known as a test in which an ultrasonic beam is transmitted from a surface of a test piece to the inside thereof to detect an ultrasonic echo reflected due to a flaw existing inside the test piece and thus estimate a size of the flaw from the loudness of the echo returned, while an amount of time elapsed from the transmission of an ultrasonic wave to the reception of the returned wave is measured to learn a distance to the position of the flaw.

For the purpose of conducting the ultrasonic flaw detection test for the test piece, an ultrasonic probe, acting as an ultrasonic transmitting and receiving unit, is employed. One end of a waveguide rod is allowed to contact with the probe via a liquid contact medium, while a contact surface of the other end of the waveguide rod is allowed to contact with a surface of the test piece via a liquid contact medium. An ultrasonic sound wave emitted from a vibrator of the probe travels in a straight line inside the waveguide rod and then reflects off a boundary surface of the flaw existing inside the test piece. Then, the ultrasonic wave, being an echo thus reflected and returned from the boundary surface, is received by the probe. The position of the flaw can be detected based on differences in time taken from the transmission of the ultrasonic waves to the reception thereof, and even if the test piece is at a high temperature, the flaw detection test can be conducted (e.g., refer to patent document 1).

In this manner, employing the waveguide rod enables diagnoses to be performed for in-service equipments such as steam pipes in electric power plants with which no probe is allowed to directly contact as well as for parts that are being processed and may reach a high temperature during their production processes.

According to the conventional art described above, however, employing the waveguide rod has caused such problem that a noise echo (sometimes, referred to as a trailing echo) obtained by the probe becomes too large. Specifically, unwanted noise echoes arise which interfere with the flaw detection by the reflection and mode conversion of an ultrasonic wave on a columnar surface of the waveguide rod.

As discussed above, according to the conventional waveguide rod, noise echoes arise on the columnar surface of the waveguide rod due to the reflection and mode conversion of an ultrasonic wave. Particularly, when an ultrasonic wave is emitted from the central position of the waveguide rod whose cross-sectional shape is circular, echoes, which have repeated the reflections and the mode conversions on the columnar surface, return to the probe, causing the noise echoes to arise. These noise echoes pose a major impediment to a pulse echo method used frequently for the ultrasonic flaw detection and hence it is craved to eliminate or alleviate the noise echoes.

Referring to the above patent document 1, it is disclosed therein that a waveguide rod comprises an externally threaded portion, a straight columnar portion, a right circular truncated cone portion and a plurality of independent minute depressions or protrusions formed on an outer circumferential surface of the right circular truncated cone, whereby ultrasonic waves inside the waveguide rod that do not enter a test piece are allowed to reflect off the depressions or the protrusions in a turbulent state, thereby preventing them from returning to a probe, thus reducing the loudness of the noise echo, i.e., the energy level thereof. Patent document 1: Japanese patent publication No. 3587555

DISCLOSURE OF THE INVENTION

Problems to be Solved by the Invention

According to the conventional art of the above patent document 1, however, there are provided the right circular truncated cone portion formed on a distal end of the waveguide rod in a manner getting gradually smaller in diameter from one end to the other, depressions and protrusions formed on an outer circumferential surface of that portion, and the externally threaded portion formed on one end of the portion. Hence, the processing of the waveguide rod becomes complicated. For example, the waveguide rod is arranged with a probe on its one end and a test piece contacts with the other end of the waveguide rod and therefore both the end faces of the waveguide rod must be precisely finished, leading to inferior workability due to the fact that in the waveguide rod described above, after having processed the right-truncated-cone-shaped portion, the other end face must be processed with a given degree of precision.

Further, the waveguide rod disclosed in the patent document 1 involves an additional problem that the intensity of an ultrasonic wave decreases due to a decrease in cross-sectional area of the right circular truncated-cone portion.

Figure 14A:
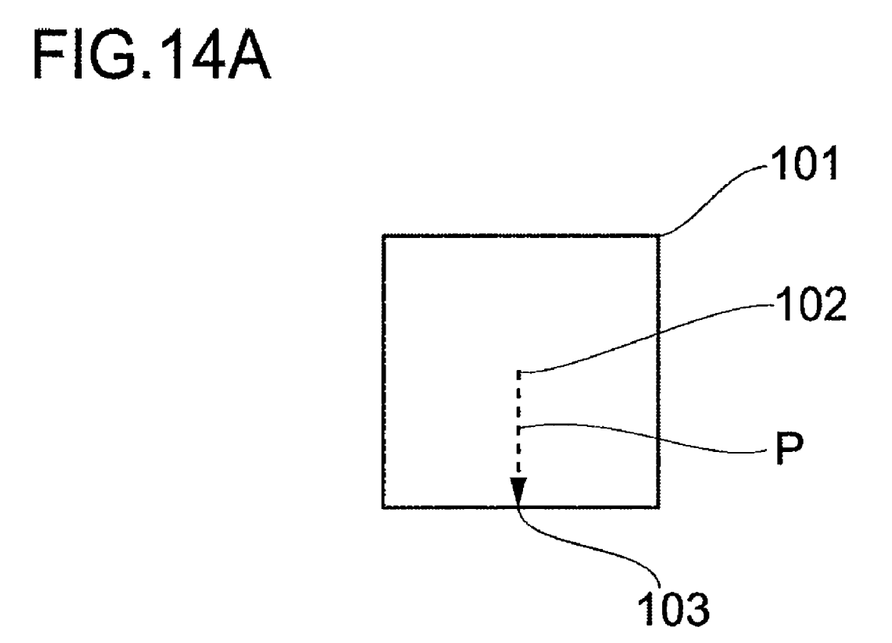
FIG. 14 is a cross-sectional view of a waveguide rod whose cross-sectional shape is a square.
Figure 14B:
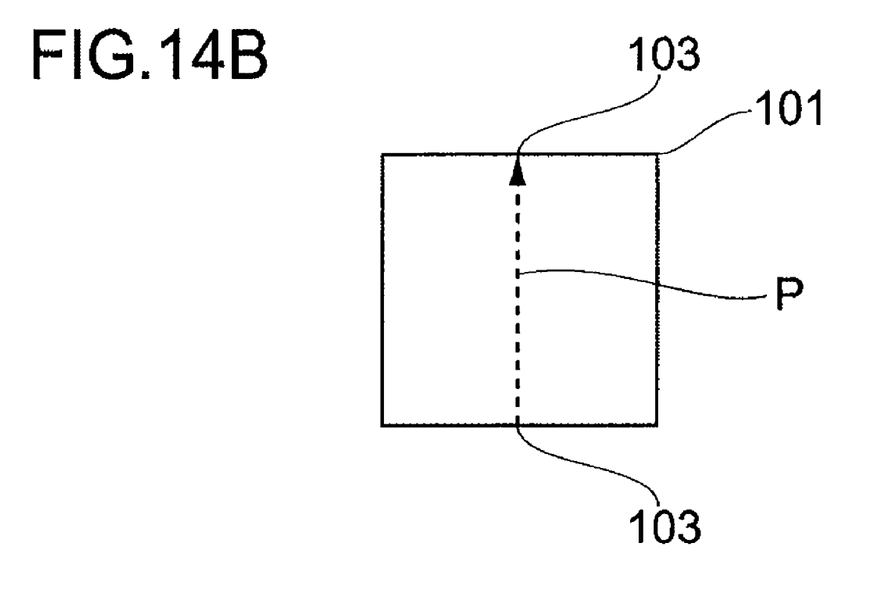
Figure 15:
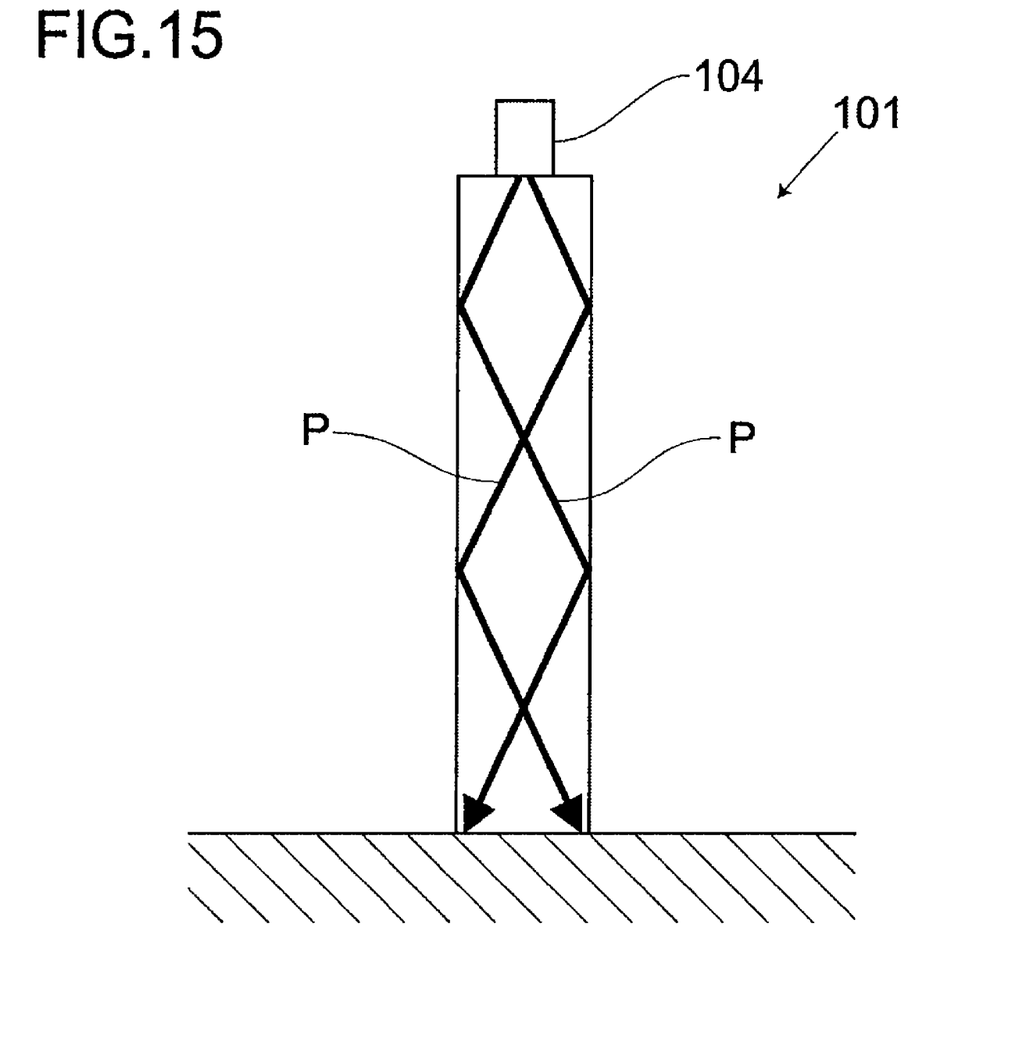
FIG. 15 is an overall cross-sectional explanatory view of a device equipped with a waveguide rod whose cross-sectional shape is that shown in FIG. 14.

Then, although not publicly made knowledgeable yet, it is schemed, as shown in FIG. 14, that a cross-sectional shape of the waveguide rod 101 is formed in a quadrangle shape different from a circle. Even if the cross-sectional shape is formed in such a quadrangle shape, however, an ultrasonic wave P emitted from the center 102 of one end still generates noise echoes, due for example to its repeating reflections and mode changes at outer surface positions 103 opposed to each other with the center 102 sandwiched therebetween and then returning to the probe or repeating reflections at other positions and returning to the probe. Giving a supplementary explanation for this phenomenon with reference to FIG. 15, the probe 104 for emitting the ultrasonic wave P is provided on one end of the waveguide rod 101 having a cross-sectional shape shown in FIG. 14, so that two ultrasonic waves P (noise echoes), subjected to the mode changes between the parallel outer surfaces, both proceed while repeating reflections until they reach an end face on the other side, at which both the two ultrasonic waves are in phase to each other to allow noise echoes to appear in their intense states, causing the noise echoes to be markedly generated in the shape with such parallel outer surfaces as the above.

Therefore, it is an object of the present invention to provide an ultrasonic measurement waveguide rod and an ultrasonic measurement instrument which are easy to manufacture and are capable of preventing a noise echo from arising.

Means for Solving the Problems

A first aspect of the present invention is an ultrasonic measurement waveguide rod having a transmitting and receiving unit arranged on one end thereof in an axial direction and a contact surface formed on the other end thereof, said contact surface being to be brought into contact with a test piece, wherein a cross-sectional shape of said ultrasonic measurement waveguide rod perpendicular to said axial direction is a polygon having sides either one of which is not parallel to any of the other sides.

A second aspect of the present invention is an ultrasonic measurement waveguide rod whose cross-sectional shape is a polygon with four or more angles.

A third aspect of the present invention is an ultrasonic measurement waveguide rod whose cross-sectional shape is a polygon with odd-numbered angles.

A fourth aspect of the present invention is an ultrasonic measurement waveguide rod, wherein none of the sides of said cross-sectional shape is parallel to each other.

A fifth aspect of the present invention is an ultrasonic measurement waveguide rod whose cross-sectional shape is asymmetric.

A sixth aspect of the present invention is an ultrasonic measurement waveguide rod whose cross-sectional shape is a pentagon.

A seventh aspect of the present invention is an ultrasonic measurement waveguide rod whose cross-sectional shape is a regular pentagon.

An eighth aspect of the present invention is an ultrasonic measurement waveguide rod whose cross-sectional shape is a polygon with nine or less angles.

A ninth aspect of the present invention is an ultrasonic measurement waveguide rod whose cross-sectional shape is the same in a partial length of the waveguide rod in said axial direction.

A tenth aspect of the present invention is an ultrasonic measurement waveguide rod whose cross-sectional shape is the same over an entire length of the waveguide rod in the axial direction.

An eleventh aspect of the present invention is an ultrasonic measurement waveguide rod, wherein said cross-sectional shape is of a similar shape over a partial or an entire length of the waveguide rod in said axial direction such that said waveguide rod is tapered.

A twelfth aspect of the present invention is an ultrasonic measurement instrument including said ultrasonic measurement waveguide rod according to any one of the foregoing aspects 9 to 11 and a transmitting and receiving unit.

Effects of the Present Invention

The conventional waveguide rod with a circular cross-sectional shape generates noise echoes due to the reflections and mode changes of an ultrasonic wave on a columnar surface of the waveguide rod.

According to the ultrasonic measurement waveguide rod of the first aspect of the invention, however, at least a pair of opposed sides are not parallel to each other and therefore an ultrasonic wave is allowed to reflect off outer surfaces making up the non-parallel sides, thus preventing them from returning to the transmitting and receiving unit as noise echoes. In other words, between the outer surfaces making up sides not parallel to one another, for example, ultrasonic wave components which have reflected perpendicularly off one outer surface are allowed to reflect off the other outer surface to thereby change their reflection angles, so that the ultrasonic waves, which have reflected off the outer surfaces making up the non-parallel sides are allowed to travel toward an outer surface of another side. Therefore, the ultrasonic waves become less likely to return to the transmitting and receiving unit and the ultrasonic waves subjected to a mode change on the outer surface do not become sterically symmetric. Hence, two ultrasonic waves do not come in phase on an end face such as a contact surface of the other end, thus giving rise to few noise echoes.

Also, as the cross-sectional shape is a polygon, the processing of the waveguide rod becomes easy in its manufacturing process and besides such waveguide rod can be easily held and put on a test piece.

Further, according to the waveguide rod of the second aspect, a large cross-sectional area of the waveguide rod per a unit circle can be secured. Hence, a reduction in ultrasonic wave can be decreased inside the waveguide rod.

In other words, when comparing areas of polygons that are capable of being placed into a reference circle having the same area, a larger effective cross-sectional area, serving as a passage of an ultrasonic wave, can be ensured in a quadrangle than in a triangle. In addition, since a regular polygon is inscribed in the reference circle, it has advantageously a larger effective area than does an inequilateral polygon.

Furthermore, according to the ultrasonic measurement waveguide rod of the third aspect, in a cross-sectional area of a regular polygon with odd-numbered angles, none of the opposed sides are parallel to one another. Hence, in an approximate polygon with odd-numbered angles, an ultrasonic wave reflects off the outer surfaces making up opposed sides not parallel to one another.

Moreover, according to the ultrasonic measurement waveguide rod of the fourth aspect, none of the opposed sides are parallel to one another. Hence, a noise echo can be prevented from returning to the transmitting and receiving unit.

Besides, according to the waveguide rod of the fifth aspect, between the outer surfaces making up symmetry sides, two waves subjected to the mode conversion on these outer surfaces become sterically twisted, alleviating the mutual reinforcement of the two waves. The two waves, however, exhibit sterically and mutually symmetric reflection behavior and therefore become slightly in phase with each other, resulting in the appearance of a slight noise echo in some cases. Contrarily, by making the cross-sectional shape asymmetry, the two waves do not exhibit the sterically and mutually symmetric reflection behavior, thus enabling a noise echo to be prevented.

Further, according to the ultrasonic measurement waveguide rod of the sixth and seventh aspects, a noise echo is prevented from arising and besides an effective cross-sectional area for serving as a passage of an ultrasonic wave can be enlarged. In a regular pentagon in particular, its effective area is large and besides when setting the waveguide rod, the outer surfaces serve as a reference, leading to easiness in handling the waveguide rod.

Furthermore, according to the waveguide rod of the eighth aspect, when a cross-sectional shape is a polygon with ten or more angles, the cross-sectional shape becomes near to a circle to reduce a restrictive effect on a noise echo. Hence, a polygon with nine or less angles is desirable.

Moreover, according to the ultrasonic measurement waveguide rod of the ninth aspect, in part of the axial direction of the waveguide rod, an ultrasonic wave reflects off the outer surfaces not parallel to one another. Hence, a noise echo can be prevented from arising.

Besides, according to the ultrasonic measurement waveguide rod of the tenth aspect, in the axial entire length of the axial direction, an ultrasonic wave reflects between the outer surfaces to permit a noise echo to be more effectively prevented from arising. Further, the cross-sectional area is constant and therefore an ultrasonic wave signal is less reduced inside the waveguide rod 2.

Further, according to the ultrasonic measurement waveguide rod of the eleventh aspect, in at least part of the axial direction of the waveguide rod, an ultrasonic wave reflects off the outer surfaces which are tapered and are not parallel to one another, thus enabling a noise echo to be prevented from arising.

Furthermore, according to the ultrasonic measurement instrument of the twelfth aspect, an ultrasonic measurement instrument can be obtained which is easy to manufacture and is equipped with the waveguide rod capable of preventing a noise echo.

BEST MODE FOR CARRYING OUT THE INVENTION

Hereunder is a detailed description of preferred embodiments of the present invention with reference to accompanying drawings. In addition, the embodiments described below do not limit the subject matter of the invention set forth in the claims. Further, all the schemes described below are not necessarily essential requirements of the present invention. In each embodiment, by adopting an ultrasonic measurement waveguide rod different from the conventional rod, a unique ultrasonic measurement waveguide rod can be obtained and then the unique ultrasonic measurement waveguide rod and an ultrasonic measurement instrument are each described.

(1) Embodiment 1

Hereunder, a description is given for an embodiment 1 of the present invention with reference to FIG. 1 to FIG. 11.

Figure 1:
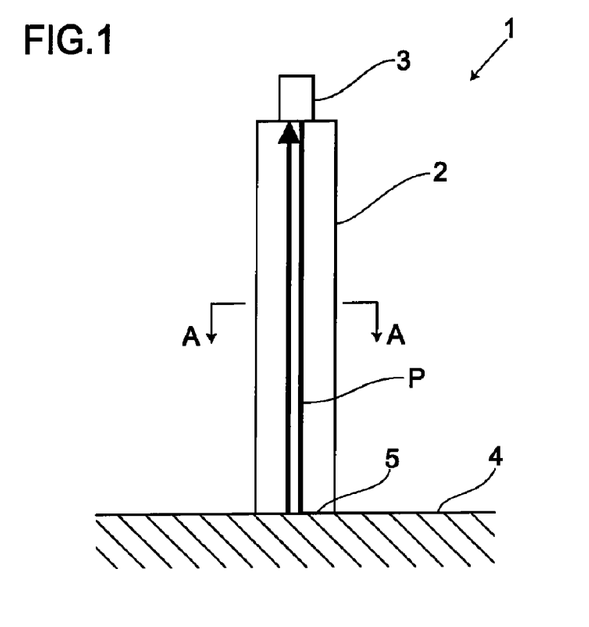
FIG. 1 is an overall diagram of a device illustrating an embodiment 1 of the present invention.

As shown in FIG. 1, an ultrasonic flaw detection instrument 1, serving as an ultrasonic measurement instrument, includes an ultrasonic flaw detection waveguide rod 2, serving as an ultrasonic measurement waveguide rod 2, and a probe 3 for acting as an ultrasonic transmitting and receiving unit, thus conducting an ultrasonic flaw detection test on various test pieces 4.

The probe 3 is arranged via a contact medium on one axial end of the waveguide rod 2 to come in contact with the one end. The ultrasonic probe 3 includes a vibrator (not shown) for generating an ultrasonic pulse and allows an ultrasonic wave emitted from the vibrator to enter a test piece via the waveguide rod 2 and then detects a returned ultrasonic wave. So, the ultrasonic probe 3 is equipped with functions of a wave transmission means and wave reception means. An ultrasonic wave P generated from the vibrator in the probe 3 to be transmitted is applied to the test piece 4 from a contact surface 5 formed in the other end of the axial direction of the waveguide rod 2. Then, an echo, being an ultrasonic wave which had reflected off a flaw inside the test piece 4 and has returned is received. As a result, the position of the flaw can be measured by an amount of time required for the transmitted ultrasonic wave to be received.

The waveguide rod 2 may be made of a metal such as aluminum, copper, stainless steel or the like, otherwise may be made of synthetic resin such as acrylic resin and may be made of other materials.

Next is a description of a characteristic structure of the waveguide rod 2.

Figure 2:
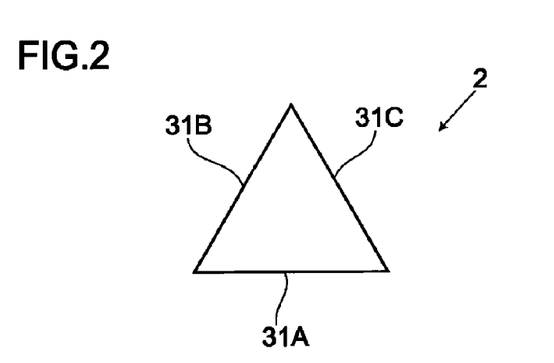
FIG. 2 is a cross-sectional view of a waveguide rod whose cross-sectional shape is a triangle.

In FIG. 2, a triangle is shown which is applied to a cross-sectional shape perpendicular to the axial direction of the waveguide rod 2. In addition, the cross-sectional shape is shown in the cross-sectional surface on a line A-A in FIG. 1. This triangular waveguide rod 2 includes three sides 31A, 31B, 21C and any of these sides 31A, 31B, 21C are not parallel to one another. The cross-sectional shape has the same size over the entire length of the waveguide rod 2, resulting in a triangle any one of whose sides is not parallel to one another. In FIG. 2, a regular triangle is shown, but is not necessarily limited to a regular triangle.

Figure 3:
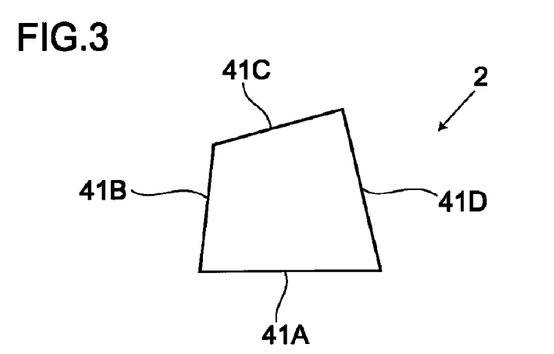
FIG. 3 is a cross-sectional view of a waveguide rod whose cross-sectional shape is a quadrangle.

In FIG. 3, a quadrangle is shown which is applied to the cross-sectional shape perpendicular to the axial direction of the waveguide rod 2. The quadrangular waveguide rod 2 includes four sides 41A, 41B, 41C, 41D. The side 41A is not parallel to the side 41C opposed to the side 41A, the side 41B is not parallel to the side 41D opposed to the side 41B. In this manner, any of the sides 41A, 41B, 41C, 41D are not parallel to one another. Besides, the side 41A is not parallel to the other sides 41B, 41C, 41D and the side 41B is not parallel to the other sides 41A, 41C, 41D. Thus, the cross-sectional shape is a quadrangle any one of whose sides is not parallel to the other sides. In addition, in the case of a polygon whose cross-sectional shape has four or more sides, any one of the sides must be parallel to the other sides except for an adjacent side.

Figure 4A:
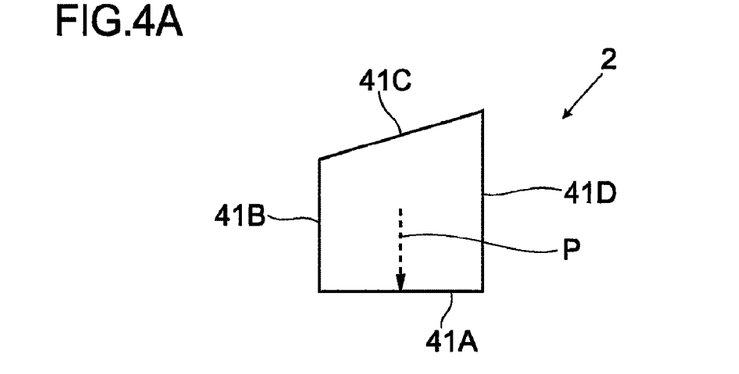
FIG. 4 is a cross-sectional view of a waveguide rod whose cross-sectional shape is a different quadrangle.
Figure 4B:
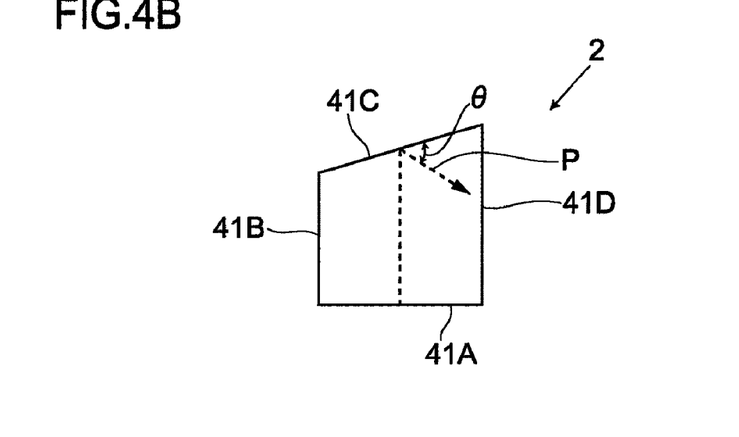
Figure 10:
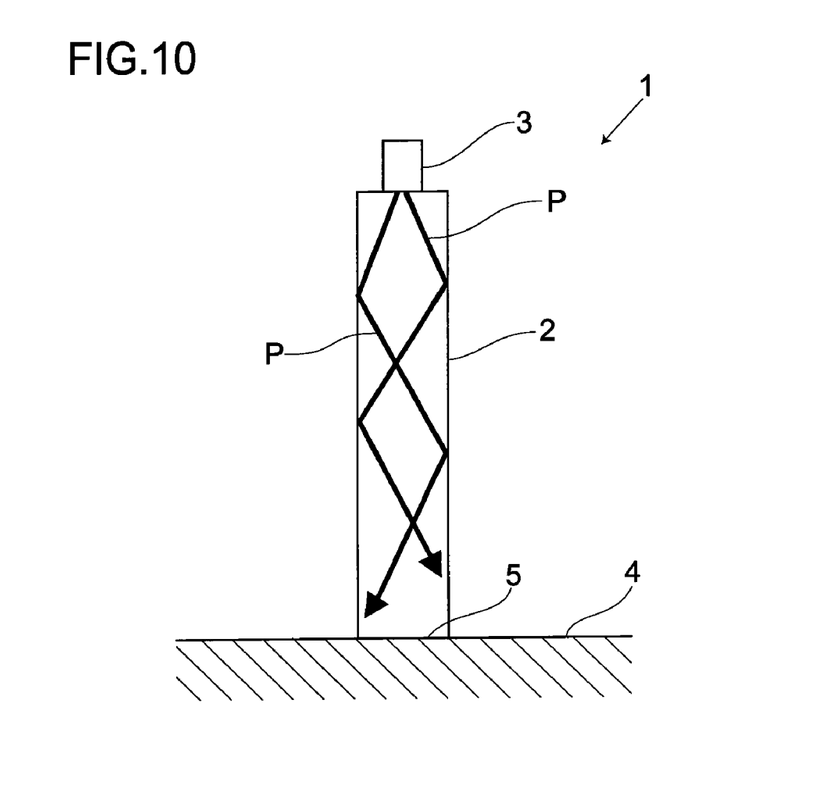
FIG. 10 is an explanatory overall cross-sectional diagram of a device equipped with a waveguide rod having a cross-sectional shape shown in FIG. 4.

In FIGS. 4(A), 4(B), FIG. 10, a different example of a waveguide rod is shown in which the cross-sectional shape perpendicular to the axial direction of the waveguide rod 2 is a different quadrangle from the above quadrangle.

In the quadrangular waveguide rod 2, a side 41A is not parallel to a side 41C opposed to the side 41A and a side 41B is parallel to a side 41D opposed to the side 41B, resulting in a quadrangle with a cross-sectional shape where any one of the sides is not parallel to the other sides.

Here, one example of reflection between outer surfaces of the side 41A and side 41C which are not parallel to each other is set forth. As shown in FIG. 4(A), an ultrasonic wave P proceeding perpendicularly to an outer surface of one side 41A from the center reflects in a backward direction to proceed to an outer surface of the other side 41C and afterward as shown in FIG. 4(B), the ultrasonic wave P reflects off the outer surface at a reflection angle θ to turn around. Accordingly, the ultrasonic wave P is led to reflect off the outer surface of a different side without repeating reflections and mode conversions between the outer surfaces of both the sides 41A, 41C, thus being prevented from returning to the probe 3 as a noise echo. In this manner, by including the outer surfaces making up sides not parallel to one another, two ultrasonic waves subjected to the mode conversion on the outer surfaces do not become sterically symmetric, as shown in FIG. 10, to get out of phase from each other on an end face such as the contact surface 5 of the other end, leading to a difficulty in observing a trailing echo.

Figure 5:
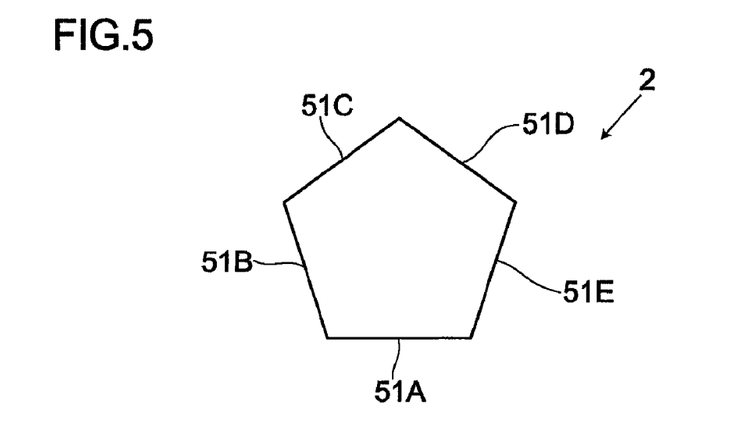
FIG. 5 is a cross-sectional view of a waveguide rod whose cross-sectional shape is a pentagon.

As a preferred example in particular, in FIG. 5, a pentagon is shown which is applied to the cross-sectional shape perpendicular to the axial direction of the waveguide rod 2. This pentagonal waveguide rod 2 includes five sides 51A, 51B, 51C, 51D, 51E and one side 51A is not parallel to the other sides 51B, 51C, 51D, 51E, one side 51B is not parallel to the other sides 51A, 51C, 51D, 51E, one side 51C is not parallel to the other sides 51A, 51B, 51D, 51E, one side 51D is not parallel to the other sides 51A, 51B, 51C, 51E, and one side 51E is not parallel to the other sides 51A, 51B, 51C, 51D. In sum, the cross-sectional shape is a regular pentagon any one of whose sides is not parallel to the other sides.

Accordingly, a radiant ray P radiated roughly from the center of one end of the waveguide rod 2 reflects off the outer surface of the waveguide rod 2 to turn in a direction different from the incident direction and reflects irregularly between these outer surfaces thus preventing the radiant ray P from returning to the probe 3 as a noise echo.

Besides, by forming the waveguide rod 2 into the cross-sectional shape of a regular polygon, the waveguide rod 2 becomes easy to set.

Figure 6:
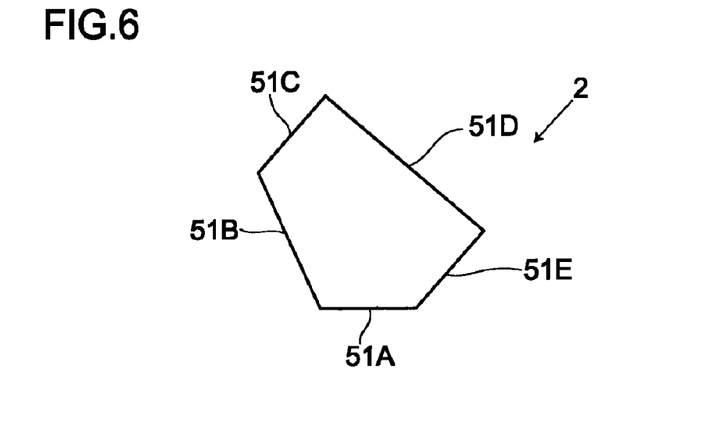
FIG. 6 is a cross-sectional view of a waveguide rod whose cross-sectional shape is a different pentagon.

In FIG. 6, a pentagon is shown which is applied to the cross-sectional shape perpendicular to the axial direction of the waveguide rod 2. In this pentagonal waveguide rod 2, sides 51A, 51B, 51E are the same as those of the regular pentagon described above and the sides 51C, 51D are different from those of the above regular pentagon and further the sides 51C, 51E are parallel to each other. This waveguide rod 2 is also formed of a pentagon whose cross-sectional shape has the sides not parallel to one another except only the pair of the sides 51C and 51E are parallel.

Figure 7:
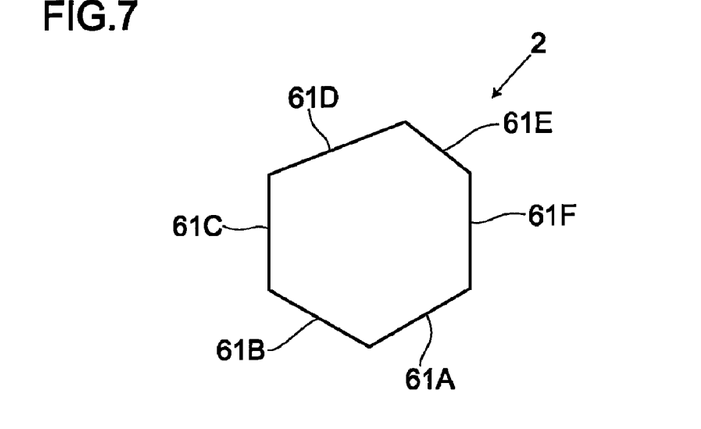
FIG. 7 is a cross-sectional view of a waveguide rod whose cross-sectional shape is a hexagon.

In FIG. 7, a hexagon is shown which is applied to the cross-sectional shape perpendicular to the axial direction of the waveguide rod 2. The hexagonal waveguide rod 2 includes six sides 61A, 61B, 61C, 61D, 61E, 61F. The side 61A is not parallel to the other sides 61B, 61C, 61D, 61E, 61F and the side 61B s not parallel to the other sides 61A, 61C, 61D, 61E, 61F and further the sides 61C, 61F are parallel to each other. Then, the sides 61A, 61B, 61C, 61F are equal in length. Besides, an angle (60 degrees) between the side 61A and the side 61B, an angle (60 degrees) between the side 61B and the side 61C, and an angle (60 degrees) between the side 61F and the side 61A are equal to one another and these angles are different from the remaining three angles between sides. In sum, the sides 61A, 61B, 61C, 61F are the same as those of a regular hexagon, while the sides 61D, 61E are different from those of a regular hexagon. Accordingly, the above cross-sectional shape is an inequilateral hexagon one of whose side 61A is not parallel to the other sides 61B, 61C, 61D, 61E, 61F.

Figure 8:
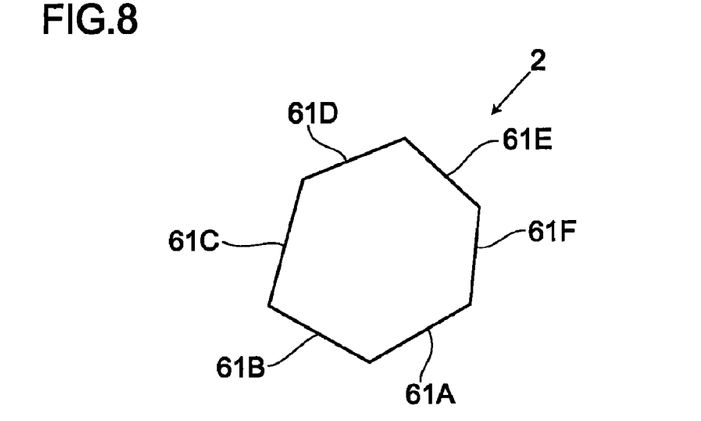
FIG. 8 is a cross-sectional view of a waveguide rod whose cross-sectional shape is a different hexagon.

In FIG. 8, a hexagon with a different shape is shown which is applied to the cross-sectional shape perpendicular to the axial direction of the waveguide rod 2. In the hexagonal waveguide rod 2, sides 61A, 61B are the same as those of a regular hexagon, while the other sides 61C, 61D, 61E, 61F are different from those of a regular hexagon. Therefore, none of the sides 61A, 61B, 61C, 61D, 61E, 61F in the cross-sectional shape are parallel to one another.

Figure 9:
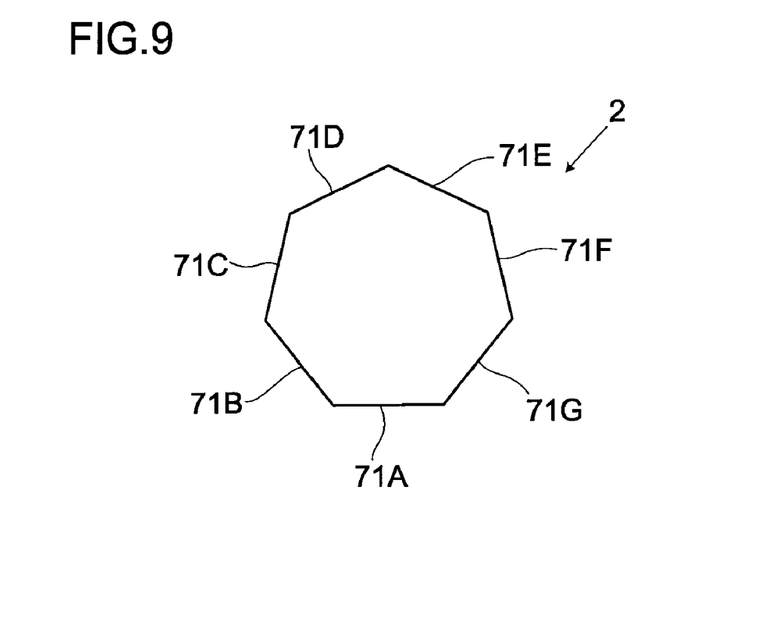
FIG. 9 is a cross-sectional view of a waveguide rod whose cross-sectional shape is a heptagon.

In FIG. 9, a heptagon is shown which is applied to the cross-sectional shape perpendicular to the axial direction of the waveguide rod 2. The heptagonal waveguide rod 2 includes seven sides 71A, 71B, 71C, 71D, 71E, 71F, 71G. All the sides 71A, 71B, 71C, 71D, 71E, 71F, 71G are not parallel to one another. The cross-sectional shape is a regular heptagon any one of whose sides is not parallel to the other sides.

Figure 11:
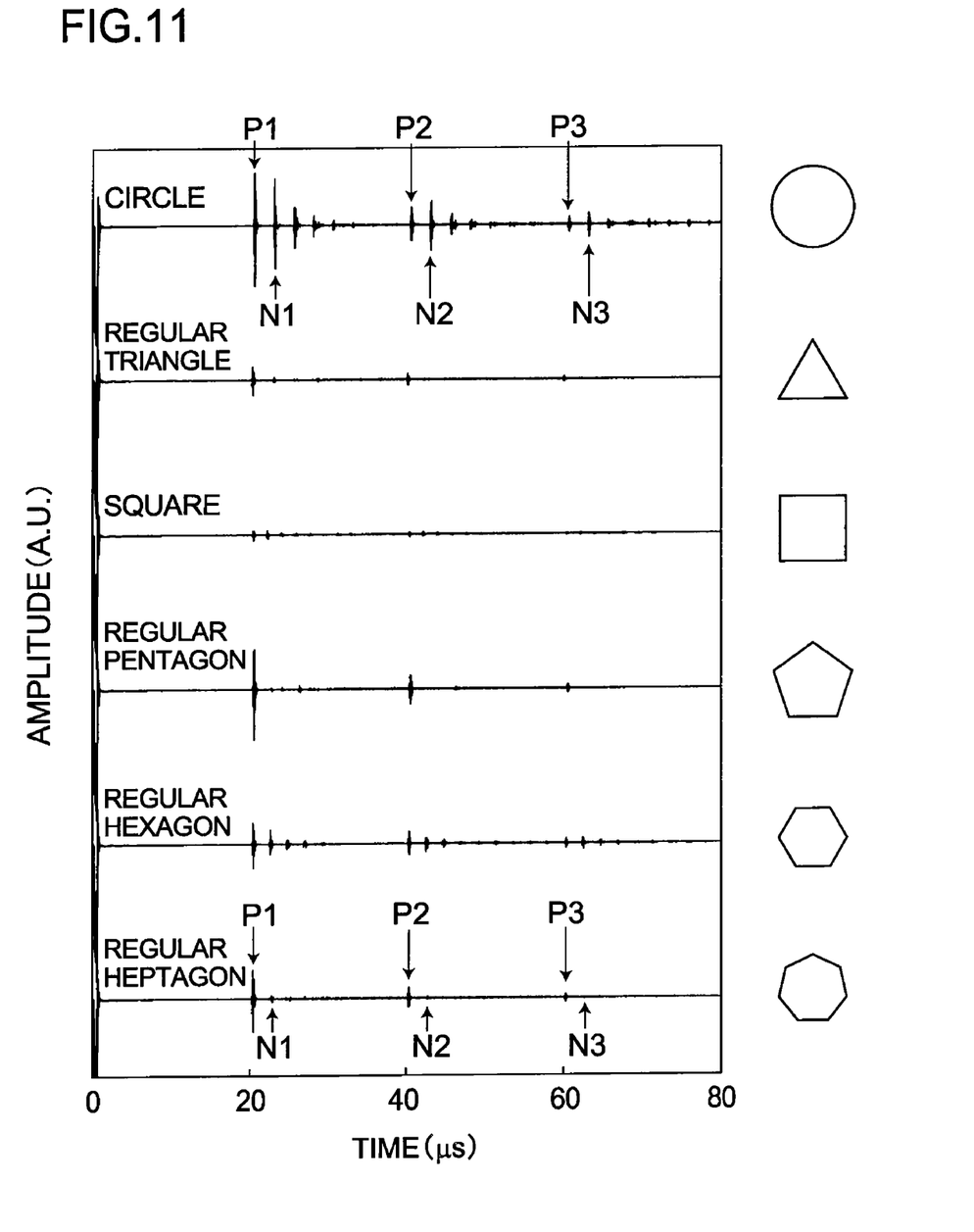
FIG. 11 is an explanatory graph illustrating an ultrasonic echo and a noise echo measured for each cross-sectional shape.

Next is a description of experimental examples. FIG. 11 is a diagram showing experimental results in which it was measured how an ultrasonic echo changed depending on a difference in cross-sectional shape of the waveguide rod 2. Amplitude is set on an ordinate axis and time is set on an abscissa axis. Corresponding to each of the cross-sectional shapes shown at the right side of the diagram in a multiple-stage manner, measured data under the same conditions are described in a multiple-stage manner. In addition, the cross-sectional shapes are a circle, a regular triangle, a square, a regular pentagon, a regular hexagon and a regular heptagon, beginning at the top.

In FIG. 11, the times 20, 40, 60 psec correspond to the ultrasonic echoes P1, P2, P3 to be measured, respectively and symbols N1, N2, N3 other than these symbols denote echo noises. In the case of a circle, in particular, several noise echoes markedly appear in retard of each of the times described above.

Hereunder, descriptions are given from the top stage of the diagram. In the case of the waveguide rod whose cross-sectional shape is a circle, the noise echo N1 with an approximately the same amplitude as that of the ultrasonic wave echo P1 to be measured is generated and besides after the ultrasonic echo P2 of the time 40 psec had reached, a noise echo with a higher amplitude than that of P2 was discernible.

In the case of the waveguide rod whose cross-sectional shape is a triangle, a noise echo N1 was sufficiently small in relation to the ultrasonic echo P1, proving for the noise echo to have a less effect on the ultrasonic echo. In this case, the intensity ratio between the ultrasonic wave echo P1 and the noise echo N1 (amplitude of the ultrasonic wave echo P1/amplitude of the noise echo N1) is approximately "5". Then, the lager the intensity ratio, the smaller the effect of the noise echo, thus permitting precise measurement to be implemented.

In the case of the waveguide rod whose cross-sectional shape is a square, on the diagram, the amplitude of the noise echo N1 is small. The amplitude of the ultrasonic wave echo P1, however, is nearly equal to that of the noise echo N1, thus resulting in the large effect of the noise echo N1. In this case, the intensity ratio between the ultrasonic wave echo P1 and the noise echo N1 becomes approximately "1".

In the case of the waveguide rods whose cross-sectional shapes are a regular pentagon and a regular heptagon, an echo noise scarcely appears and in the case of a regular pentagon in particular, it is learnt that the noise echo is extremely small. Then, in case of the heptagon, the intensity ratio between the ultrasonic wave echo P1 and the noise echo N1 is approximately "10". So, it is learnt that the intensity ratio of the regular pentagon is further larger than that of the regular heptagon.

In the case of the waveguide rod whose cross-sectional shape is a regular hexagon, it is learnt that the effect of the noise echo is larger as compared to that of the regular pentagon and the regular heptagon, In this case, the intensity ratio between the ultrasonic wave echo P1 and the noise echo N1 is approximately "2".

These cases are the experimental results when the cross-sectional shapes are a circle and regular polygons, proving the following fact from these results. As described in the background art, the waveguide rod whose cross-sectional shape is a circle has a profound effect of a noise echo. Then, the waveguide rod whose cross-sectional shape is a square causes no difference between the amplitudes of the ultrasonic wave echo P1 and the noise echo N1 and in other words, the intensity ratio is small and therefore the noise echo has a profound effect. In a similar fashion, the waveguide rod whose cross-sectional shape is a regular hexagon brings also a profound effect of the noise echo.

In addition, the above intensity ratio of echoes is an example and by varying a geometric structure such as a cross-sectional shape, an axial length or the like of the waveguide rod, the intensity ratio is further increased and eventually the effect of the noise echo can be substantially eliminated.

Contrary to these cross-sectional shapes, in a regular polygon whose cross-sectional shape has odd-numbered angles, a less noise echo is brought about to cause a slight effect. A regular pentagon in the cross-sectional shape, in particular, brought about a favorable result. A regular heptagon produces a similar effect, but a slight noise echo appears. This means that the regular heptagon is nearer to a circle than is the regular pentagon, thus leading to a reduction in effect of preventing a noise echo from arising.

As described above, according to the present embodiment, there is provided the ultrasonic flaw detection waveguide rod 2 which is arranged with the probe 3 on one end of the axial direction of the waveguide rod 2 and is formed with the contact surface 5 coming in contact with the test piece 4 on the other end of the axial direction of the waveguide rod 2. In the ultrasonic flaw detection waveguide rod 2, its cross-sectional shape perpendicular to the axial direction is an approximate polygon any one of whose sides in the cross-sectional shape is not parallel to the other sides. Hence, at least a pair of opposed sides are not parallel to each other and therefore an ultrasonic wave reflects off the outer surfaces making up the sides not parallel to one another, thus being prevented from returning to the probe 3 as a noise echo. That is, between the outer surfaces making up the sides 41A, 41C not parallel to each other, for example, ultrasonic wave components which has reflected perpendicularly off the outer surface of one side reflects off the outer surface of the other side to be changed in its reflected angle and further an ultrasonic wave which has reflected on the outer surface making up the sides 41A, 41C not parallel to each other heads for the outer surface 41D of the other side. Therefore, an echo, acting as a noise, is hard to return to the probe 3 and further the ultrasonic wave subjected to the mode conversions on the outer surfaces does not become sterically symmetric. Hence, two waves do not become in phase on the contact surface 5 of the other end, resulting in the generation of a slight noise echo.

Further, the waveguide rod 2 has a cross-sectional shape of a polygon. Hence, its manufacturing process becomes easy and the waveguide rod 2 is easily held and easily set on the test piece 4.

Furthermore, as described above, according to the present embodiment, the cross-sectional shape is a polygon with four or more angles. Hence, the cross-sectional area of the waveguide rod 2 per unit circle can be ensured larger, permitting an amount of the attenuation of the ultrasonic wave inside the waveguide rod 2 to be decreased. In other words, when comparing areas of polygons fitting into a reference circle of the same area with one another, an effective cross-sectional area, serving as a passage of an ultrasonic wave, can be ensured larger in a quadrangle than in a triangle. In addition, a regular polygon is inscribed in the reference circle and therefore when being compared with an inequilateral polygon, the regular polygon ensures advantageously a larger effective area than does the inequilateral polygon.

Moreover, as shown in FIGS. 3, 5, 6, 9 in the present embodiment, the cross-sectional shapes are polygons with odd-numbered angles and therefore none of the opposed sides are parallel to one another in the cross-sectional shape. Hence, in a polygon other than a regular polygon with odd-numbered angles, an ultrasonic wave reflects off the outer surfaces making up sides not parallel to one another, thus permitting a noise echo to be prevented from arising.

Besides, as described above, according to the present embodiment, as shown in FIGS. 2, 3, 5, 8, 9, none of the sides of the cross-sectional shape are parallel to one another. Hence, a noise echo can be prevented from arising.

Further, as described above, according to the present embodiment, as shown in FIGS. 3, 4, 6, 7, 8, the cross-sectional shapes are asymmetric. When the cross-sectional shape is an isosceles trapezoid or the like, two waves subjected to the mode conversions on the outer surfaces making up the symmetric sides become sterically twisted, alleviating the mutual reinforcement of the two waves. The two waves, however, exhibit sterically and mutually symmetric reflection behavior and becomes slightly in phase, resulting in the appearance of a slight noise echo in some cases. Contrarily, in the present embodiment, by making the cross-sectional shape asymmetry, the two waves do not exhibit the sterically and mutually symmetric reflection behavior, thus enabling a noise echo to be prevented.

Furthermore, as described above, in the present embodiment, the cross-sectional shape is a pentagon and besides is a regular pentagon. Hence, a noise echo is prevented from arising and besides an effective cross-sectional area, serving as a passage of an ultrasonic wave, can be enlarged. In a regular pentagon in particular, its effective area is larger and when setting the waveguide rod 2, the outer surfaces act as a reference position, leading to easiness in handling the waveguide rod 2.

Moreover, as described above, in the present embodiment, the cross-sectional shape is a polygon with nine or less angles. So, due to the fact that when the cross-sectional shape is a polygon with ten or more angles, the cross-sectional shape becomes near to a circle to reduce a restrictive effect on a noise echo, this shape of a polygon with nine or less angles is desirable. Further, when the cross-sectional shape is a circle, a pair of parallel sides exists virtually in the 360-degree direction. Hence, on the contact surface on the other end, waves become in phase, resulting in the appearance of an intense noise echo.

Besides, as described above, in the present embodiment, the cross-sectional shape is unchanged over the entire length of the axial direction, an ultrasonic wave reflects between the outer surfaces to enable a noise echo to be more effectively prevented from arising. Further, the cross-sectional area is constant, thereby leading to a less reduction in strength of an ultrasonic signal inside the waveguide rod 2.

Further, as described above, in the present embodiment, the ultrasonic flaw detection device 1 is provided with the ultrasonic waveguide rod 2 and the probe 3 which are described in any one of the aspects 1 to 11 of the present invention. Hence, the ultrasonic flaw detection device 1 can be obtained which is easy to manufacture and is equipped with the ultrasonic flaw detection waveguide rod 2 capable of preventing a noise echo from arising.

Embodiment 2

Figure 12:
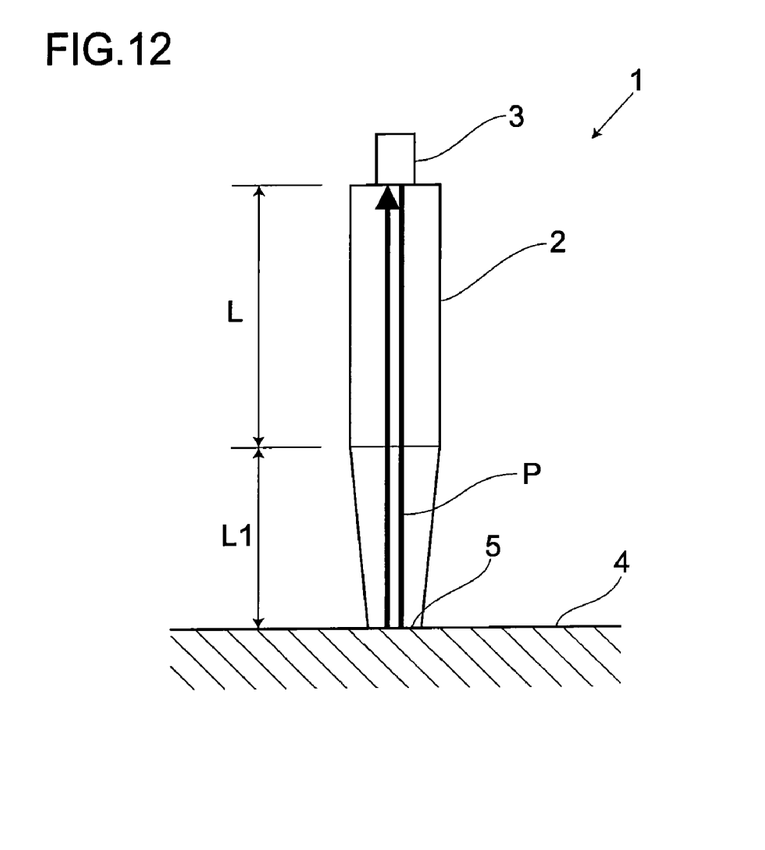
FIG. 12 is an overall diagram of a device illustrating the embodiment 2 of the present invention.

FIG. 12 shows an embodiment 2 of the present invention. Then, parts the same as in the embodiment 1 are attached with the same symbols and a detailed description thereof is given with the descriptions of the same part omitted. In this embodiment, a cross-sectional shape is formed of the same shape of a polygon in part of a length L and is formed of a tapered polygon diminishing toward the other end in cross-sectional area. Besides, the cross-sectional shape in the part of the tapered polygon is formed of a homothetic shape.

Further, as described above, in the present embodiment, the cross-sectional shape is the same in the part in the axial direction. Hence, in the part of the axial direction, an ultrasonic wave reflects off the outer surfaces not parallel to one another, thus enabling a noise echo to be prevented from arising.

Furthermore, as described above, in the present embodiment, the cross-sectional shape is formed of a homothetic shape in the part of or the entire length of the axial direction and the waveguide rod 2 is tapered. Hence, in at least the part of the axial direction, an ultrasonic wave reflects off the tapered outer surfaces not parallel to one another, thus enabling a noise echo to be prevented from arising.

Moreover, in the waveguide rod with a cross-sectional shape of a circle, part of the waveguide rod may be formed of a polygon shown in the above embodiment. In this case, in part of the polygon, at least a pair of sides opposed to each other are not parallel to each other. Hence, an ultrasonic wave reflects off the outer surfaces making up the sides not parallel to one another, thus enabling a noise echo to be prevented from arising.

Embodiment 3

Figure 13:
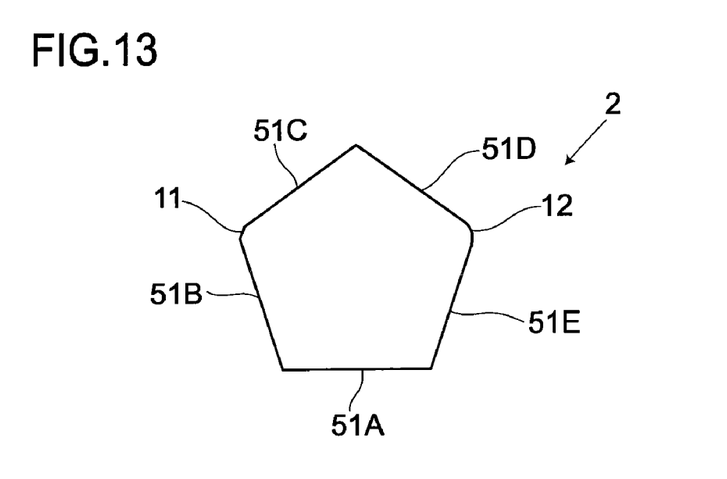
FIG. 13 is a cross-sectional view of a waveguide rod whose cross-sectional shape is a pentagon, illustrating the embodiment 3 of the present invention.

FIG. 13 shows a third embodiment of the present invention. Then, parts the same as in the above embodiments are attached with the same symbols and a detailed description is given with the descriptions of the same parts omitted. In this embodiment, the waveguide rod 2 is formed of, e.g., a regular pentagon, as a polygon. The corners of the cross-sectional shape are formed with a cutout portion 11 subjected to a chamfering process and is formed with an R-shape-processed portion 12 subjected to an R forming process. In this case, the cross-sectional shape is unchanged as a pentagon. Although the embodiments of the present invention are described in detail above, the present invention is not limited to the above embodiments and various modifications are possible within the scope of the gist of the invention. The shape of a polygon, for example, does not need to be precise but may be of an approximate polygon. Further, the present invention is not limited to the use for ultrasonic flaw detection but may be extensively applicable to "ultrasonic measurement" in general.

DESCRIPTION OF SYMBOLS

1 ultrasonic flaw detection device (ultrasonic measurement device)
2 ultrasonic flaw detection waveguide rod (ultrasonic measurement waveguide rod)
3 ultrasonic probe (ultrasonic transmitting and receiving unit)
4 test piece
5 contact surface
31A, 31B, 31C, side
41A, 41B, 41C, 41D side
51A, 51B, 51C, 51D, 51E side
61A, 61B, 61C, 61D, 61E, 61F side
71A, 71B, 71C, 71D, 71E, 71F, 71G side

The invention claimed is:

1. An ultrasonic measurement waveguide rod having a transmitting and receiving unit arranged on one end thereof in an axial direction and a contact surface formed on the other end thereof, said contact surface being to be brought into contact with a test piece, wherein said waveguide rod is elongated in said axial direction, and a cross-sectional shape of said ultrasonic measurement waveguide rod perpendicular to said axial direction is a polygon having sides either one of which is not parallel to any of the other sides.

2. The ultrasonic measurement waveguide rod according to claim 1, wherein said cross-sectional shape is a polygon with four or more angles.

3. The ultrasonic measurement waveguide rod according to claim 2, wherein none of the sides of said cross-sectional shape is parallel to each other.

4. The ultrasonic measurement waveguide rod according to claim 3, wherein said cross-sectional shape is a pentagon.

5. The ultrasonic measurement waveguide rod according to claim 4, wherein said cross-sectional shape is a regular pentagon.

6. The ultrasonic measurement waveguide rod according to claim 3, wherein said cross-sectional shape is asymmetric.

7. The ultrasonic measurement waveguide rod according to claim 2, wherein said cross-sectional shape is asymmetric.

8. The ultrasonic measurement waveguide rod according to claim 7, wherein said cross-sectional shape is a pentagon.

9. The ultrasonic measurement waveguide rod according to claim 2, wherein said cross-sectional shape is a polygon with nine or less angles.

10. The ultrasonic measurement waveguide rod according to claim 2, wherein said cross-sectional shape is a polygon with odd-numbered angles.

11. The ultrasonic measurement waveguide rod according to claim 1, wherein said cross-sectional shape is a polygon with odd-numbered angles.

12. The ultrasonic measurement waveguide rod according to claim 11, wherein none of the sides of said cross-sectional shape is parallel to each other.

13. The ultrasonic measurement waveguide rod according to claim 11, wherein said cross-sectional shape is asymmetric.

14. The ultrasonic measurement waveguide rod according to claim 11, wherein said cross-sectional shape is a polygon with nine or less angles.

15. The ultrasonic measurement waveguide rod according to claim 1, wherein said cross-sectional shape is the same in a partial length of the waveguide rod in said axial direction.

16. An ultrasonic measurement instrument, comprising said ultrasonic measurement waveguide rod according to claim 15 and a transmitting and receiving unit.

17. The ultrasonic measurement waveguide rod according to claim 1, wherein said cross-sectional shape is the same over an entire length of the waveguide rod in said axial direction.

18. An ultrasonic measurement instrument, comprising said ultrasonic measurement waveguide rod according to claim 17 and a transmitting and receiving unit.

19. The ultrasonic measurement waveguide rod according to claim 1, wherein said cross-sectional shape is of a similar shape over a partial or an entire length of the waveguide rod in said axial direction such that said waveguide rod is tapered.

20. An ultrasonic measurement instrument, comprising said ultrasonic measurement waveguide rod according to claim 19 and a transmitting and receiving unit.

* * * * *